(12) United States Patent
Corbo et al.

(10) Patent No.: US 6,663,893 B2
(45) Date of Patent: Dec. 16, 2003

(54) TASTE MASKING COATING COMPOSITION

(75) Inventors: Michael Corbo, Flemington, NJ (US); Jatin Desai, Fairport, NY (US); Mahesh Patell, Edison, NJ (US); Ronald Warrick, Sergeantsville, NJ (US)

(73) Assignee: Bristol-Myers Squibb Co., Princeton, NJ (US)

( * ) Notice: Subject to any disclaimer, the term of this patent is extended or adjusted under 35 U.S.C. 154(b) by 0 days.

(21) Appl. No.: 10/067,724

(22) Filed: Feb. 5, 2002

(65) Prior Publication Data
US 2002/0197317 A1 Dec. 26, 2002

Related U.S. Application Data

(63) Continuation-in-part of application No. 09/557,924, filed on Apr. 20, 2000, now abandoned.

(51) Int. Cl.$^7$ .............................. A61K 9/28; A61K 9/30; A61K 9/32; A61K 9/16; A61K 9/42
(52) U.S. Cl. ...................... 424/474; 424/464; 424/465; 424/474; 424/475; 424/476; 424/480; 424/482; 424/490; 424/491; 424/494
(58) Field of Search ................................ 424/451, 452, 424/464, 465, 474, 475, 476, 489, 490, 480, 482, 491, 494

(56) References Cited

U.S. PATENT DOCUMENTS

| | | |
|---|---|---|
| 3,453,360 A | 7/1969 | Hill |
| 3,520,970 A | 7/1970 | Lehmann et al. |
| 3,531,418 A | 9/1970 | Fanger et al. |
| 3,576,760 A * | 4/1971 | Gould et al. ................ 252/403 |
| 3,577,512 A | 5/1971 | Shepherd et al. |
| 3,629,392 A | 12/1971 | Banker et al. |
| 3,775,537 A | 11/1973 | Lehmann et al. |
| 3,821,422 A | 6/1974 | Morse et al. |
| 3,860,733 A | 1/1975 | Morse et al. |
| 3,909,444 A | 9/1975 | Anderson |
| 3,935,326 A | 1/1976 | Groppenbacher et al. |
| 3,959,540 A | 5/1976 | Leiberich et al. |
| 4,016,254 A | 4/1977 | Seager |
| 4,060,598 A | 11/1977 | Groppenbacher |
| 4,101,651 A | 7/1978 | Kobayashi et al. |
| 4,112,215 A | 9/1978 | Boessler et al. |
| 4,321,117 A | 3/1982 | Kaetsu et al. |
| 4,321,253 A | 3/1982 | Beatty |
| 4,330,338 A | 5/1982 | Banker |
| 4,341,759 A | 7/1982 | Bogentoft et al. |
| 4,367,217 A | 1/1983 | Gruber et al. |
| 4,411,754 A | 10/1983 | Kaetsu et al. |
| 4,433,076 A | 2/1984 | Bauer et al. |
| 4,499,066 A | 2/1985 | Moro et al. |
| 4,520,172 A | 5/1985 | Lehmann et al. |
| 4,587,118 A | 5/1986 | Hsiao |
| 4,656,027 A | 4/1987 | Sjoovist |
| 4,666,703 A | 5/1987 | Kopf |
| 4,710,384 A | 12/1987 | Rotman |
| 4,749,575 A | 6/1988 | Rotman |
| 4,760,093 A | 7/1988 | Blank et al. |
| 4,766,012 A | 8/1988 | Valenti |
| 4,800,087 A | 1/1989 | Mehta |
| 4,839,177 A | 6/1989 | Colombo et al. |
| 4,851,226 A | 7/1989 | Julian et al. |
| 4,908,214 A | 3/1990 | Bobee et al. |
| 4,916,161 A * | 4/1990 | Patell .......................... 514/570 |
| 4,968,508 A | 11/1990 | Oren et al. |
| 4,975,283 A | 12/1990 | Patell |
| 5,084,278 A | 1/1992 | Mehta |
| 5,149,542 A | 9/1992 | Valducci |
| 5,188,839 A | 2/1993 | Pearmain |
| 5,409,711 A | 4/1995 | Mapelli et al. |
| 5,472,708 A | 12/1995 | Chen |
| 5,489,436 A * | 2/1996 | Hoy et al. .................. 424/441 |
| 5,552,152 A | 9/1996 | Shen |
| 5,633,046 A | 5/1997 | Petropoulos et al. |
| 5,639,475 A | 6/1997 | Bettman et al. |
| 5,654,004 A | 8/1997 | Okayama et al. |
| 5,707,646 A | 1/1998 | Yajima et al. |
| 5,709,886 A | 1/1998 | Bettman et al. |
| 5,874,418 A * | 2/1999 | Stella et al. .................. 514/58 |
| 6,482,823 B1 * | 11/2002 | Yu et al. .................. 514/228.2 |

FOREIGN PATENT DOCUMENTS

| | | |
|---|---|---|
| EP | 0352800 A3 | 1/1990 |
| EP | 0378137 A3 | 7/1990 |
| EP | 0523847 B1 | 1/1993 |
| WO | WO 01/03698 | 1/2001 |

* cited by examiner

Primary Examiner—Thurman K. Page
Assistant Examiner—S. Tran
(74) Attorney, Agent, or Firm—Jonathan N. Provoost; Laurelee A. Duncan

(57) ABSTRACT

There is provided a coating composition that masks the undesirable taste of a pharmaceutically active ingredient, i.e. drug or medicine, that is taken orally. The coating composition is comprised of dimethylaminoethyl methacrylate and neutral methacrylic acid ester, a cellulose ester polymer, and an alkaline modifier.

23 Claims, No Drawings

TASTE MASKING COATING COMPOSITION

RELATED U.S. APPLICATION DATA

This application is a continuation-in-part of U.S. application Ser. No. 09/557,924 filed Apr. 20, 2000 now abandoned.

BACKGROUND OF THE INVENTION

1. Field of the Invention

The present invention relates to a coating applied to the outside of a pharmaceutically active ingredient. More particularly, the present invention relates to a coating that masks the taste of a pharmaceutically active ingredient.

2. Description of the Prior Art

In general, there are two types of tablet dosage forms that are available in the marketplace, one that can be swallowed as a whole entity and the other as a chewable tablet. If the tablet is swallowed whole, the unpleasant taste of the pharmaceutically active ingredient is greatly minimized or avoided altogether. However, tablets formulated in a chewable form are designed for young children and for people with difficulty swallowing. Hence, the undesirable taste of the chewable tablet is mainly due to the bad taste of the pharmaceutically active ingredient. This can ultimately create a feeling of reluctance to taking medicine.

The use of a coating as part of a medicament is known. The coating is typically applied for the ease of swallowing and provides a barrier, which prevents the undesirable taste of the drug ingredient from coming through, making the drug preparation more palatable. In addition, this type of coating can be designed to act as a time release mechanism to control the rate of release of the medicine in the body. This can be accomplished in various ways such as adjusting the thickness of the coating and selection of the coating polymers/components that are used in these types of specialized coating formulations.

Various types of coatings can be applied to the outside of tablets and drug powders to achieve a specific desired effect. Enteric coatings are designed to be soluble in the intestine, where the pH is 6.5 or higher, but insoluble in the stomach, where the pH is lower. On the other hand, reverse enteric coatings are designed to be partially soluble in the stomach, i.e. under acidic or lower pH conditions, thereby releasing the drug in the stomach. Coatings can also be used for masking purposes including taste masking of chewable products.

Several U.S. patents are directed to taste masking. However, none disclose the coating of the present invention.

U.S. Pat. No. 4,851,226 issued on Jul. 25, 1989 to Julian et al. It provides a chewable medicament tablet made from granules coated with a blend of cellulose acetate or cellulose acetate butyrate and polyvinyl pyrrolidone.

U.S. Pat. No. 5,075,114, which issued on Dec. 24, 1991 to Roche, provides a taste masking and sustained release coating applied to a tablet. The coating blend is made with cellulose acetate and/or cellulose acetate butyrate and hydroxypropyl cellulose.

U.S. Pat. No. 5,489,436 issued on Feb. 6, 1996 to Hoy et al. This patent provides chewable tablets that have a coating consisting essentially of dimethylaminoethyl methacrylate and neutral methacrylic acid ester, and a polymer selected from the group consisting of cellulose acetate, cellulose triacetate, and mixtures thereof.

SUMMARY OF THE INVENTION

It is an object of the present invention to provide a coating or coating composition that coats a pharmaceutically active ingredient or particle and, thus, is part of a medicament.

It is another object of the present invention to provide such a coating that masks the undesirable taste, without delaying the availability, of the pharmaceutically active ingredients when consumed orally.

It is also an object of the present invention to provide such a coating that is substantially insoluble in water and in a neutral pH environment, e.g. the mouth.

It is another object of the present invention to provide a medicament having the coating, which inhibits the availability of the drug ingredient in the mouth and in a pH neutral environment.

It is still another object of the present invention to provide such a coating that rapidly breaks down in an acid environment, such as in the stomach, thereby releasing the drug.

It is still another object of the present invention to provide such a coating that readily dissolves, yet the rate of dissolution can be modified based on the composition.

It is still yet another object of the present invention to provide a medicament comprising a pharmaceutical active agent and the coating.

It is still yet another object of the present invention to provide such a medicament in a variety of forms.

It is still yet another object of the present invention to provide a pharmaceutical composition comprising one or more pharmaceutical active agents coated with the coating of the present invention, which has an alkaline component in the coat composition that enhances the performance of the coat.

To accomplish the foregoing objects and advantages, the present invention, in brief summary, is a coating composition that masks the taste of a drug ingredient or medicine taken orally. The composition has (a) dimethylaminoethyl methacrylate and neutral methacrylic acid ester, (b) a cellulose ester polymer, and (c) an alkaline modifier.

DETAILED DESCRIPTION OF THE INVENTION

In the present application, a medicament is defined as a drug ingredient that is coated with a coating composition. Taste masking is understood as a perceived reduction of an undesirable taste that would otherwise be there.

The mouth is, for the most part, a neutral environment where the pH is about 7. One can mask the unpleasant taste of a drug by surrounding the drug ingredient, drug particle, or an agglomeration of drug particles with a coating composition that is insoluble in the mouth. The coating must be formulated to rapidly break down in the stomach to release the pharmaceutically active ingredient into the body. The present invention accomplishes this by providing a coating composition that effectively masks the unpleasant taste of a pharmaceutically active ingredient, i.e., drug or medicine, taken orally and immediately dissolves in an acidic pH environment, thereby releasing the pharmaceutically active ingredient in the stomach. Moreover, there is no noticeable after taste.

The coating composition of the present invention has a taste masking blend. The blend is (a) dimethylaminoethyl methacrylate and neutral methacrylic acid ester, (b) a cellulose ester polymer, and (c) an alkaline modifier.

The dimethylaminoethyl methacrylate and neutral methacrylic acid ester is a first essential component in the present coating composition. This compound is available commercially from Rohm Pharma, and is sold under the tradename EUDRAGIT® E 100. EUDRAGIT® E 100 is supplied as colorless to yellow tinged granules with a characteristic amine-like odor. The structural formula is:

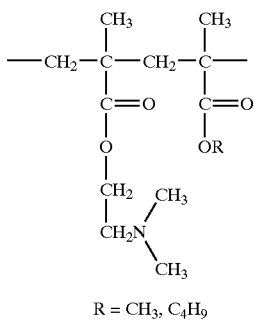

R = CH₃, C₄H₉

The dimethylaminoethyl methacrylate and neutral methacrylic acid ester is known to be soluble in acidic environments where the pH is up to about 5. At a pH greater than about 5, the ester is insoluble in water. Thus, the ester is relatively insoluble in the mouth where the pH is about 7.

The dimethylaminoethyl methacrylate and neutral methacrylic acid ester is in the present coating composition in an amount about 3 percentage by weight or weight percent (wt. %) to about 97 wt. % of the total coating composition. Preferably, the dimethylaminoethyl methacrylate and neutral methacrylic acid ester is about 10 wt. % to about 40 wt. % of the total weight of the coating composition. The level of the dimethylaminoethyl methacrylate and neutral methacrylic acid ester that is included in the coating composition is determined by considering the cost of the raw material and the desired dissolution rate. For example, below about 10 wt. %, the dimethylaminoethyl methacrylate and neutral methacrylic acid ester does not dissolve as well as within the preferred range. Above 40 wt. %, the cost of this ingredient starts to become cost prohibitive.

A second essential component of the present coating composition also includes a cellulose ester polymer. For the most part, the cellulose ester polymer is insoluble in water. This insolubility property enables the cellulose ester polymer to inhibit dissolution of the medicament in the mouth. The cellulose ester polymer may be, for example, cellulose acetate (CA), cellulose acetate butyrate, cellulose acetate triacetate, cellulose proprionate, ethyl cellulose, or mixtures thereof. The preferred cellulose ester polymers are cellulose acetate and ethyl cellulose.

The cellulose ester polymer is present in the present coating composition in an amount about 3 wt. % to about 97 wt. %. Preferably, the cellulose ester polymer is about 25 wt. % to about 90 wt. %. Most preferably, the cellulose ester polymer is about 50 wt. % to about 80 wt. %. The cellulose ester polymer is a relatively inexpensive raw material. Accordingly, it is included over other essential components in the coating composition at relatively high levels. This component exhibits maximum solubility above the lower limits of its most preferred range.

The alkaline modifier is the third essential component in the coating composition of the present invention. This component serves several functions. It acts as a stabilizer, buffering the microenvironment of the coating to a neutral pH, which enhances the coating integrity over coatings that do not have an alkaline modifier. This coating integrity improves the storage stability in a dry state and in a liquid suspension. The alkaline modifier also functions as a plasticizer to reduce the brittleness of the coating. The alkaline modifier may also serve to decrease the dissolution rate of the coated tablets in the mouth thereby enhancing the taste masking effect of the coating.

Moreover, the alkaline modifier serves as a release agent that increases the speed of dissolution of the coating in the acidic environment of the stomach (pH 1.2). Accordingly, the drug ingredient is delivered more rapidly in the stomach than is a drug coated with a like coating composition that does not contain an alkaline modifier in it. The alkaline modifier enhances the dissolution rate of the coating and, consequently, increases the release rate of the drug in the stomach. Preferably, the alkaline modifier enables substantially complete release of the drug in the stomach.

Suitable alkaline modifiers are, for example, triethanolamine (TEA), basic amino acids, talc, ammonium oleate, meglumine, trimethylamine, calcium silicate, aluminum magnesium silicate, food alkalizing agents commonly used in the food industry, or mixtures thereof. The basic amino acids can be, for example, L-argenine, L-histadine, prolamine, or mixtures thereof. In addition, aluminum magnesium silicate may also be used in the present invention as an alkaline modifier.

An effective amount of the alkaline modifier is in the present coating composition. What is an effective amount varies according to the desired dissolution rate. In one embodiment, the alkaline modifier is about 0.2 wt. % to about 20 wt. % of the coating composition. Preferably, the alkaline modifier is about 1 wt. % to about 15 wt. %. If the alkaline modifier is included at too high a level, the integrity of the coating may be adversely effected.

The present coating composition may also have other components or additives. The additives may include, for example, 2-vinyl pyridine (V)/styrene (S) copolymer, diluents, fillers, bulking agents, pigments, opacifiers, other plasticizers including polyvinylpyrrolidone (PVP), or mixtures thereof. The polymer weight ratio of V to S in the 2-vinyl pyridine (V)/styrene (S) copolymer is preferably about 65/35 or 80/20.

In a preferred embodiment, the present invention is a medicament having a drug or active ingredient and a coating composition for masking the taste of the drug ingredient. The preferred coating composition has (a) dimethylaminoethyl methacrylate and neutral methacrylic acid ester, (b) a cellulose ester polymer, and (c) a alkaline modifier. The ratio of the coating composition to active ingredient is about 1:50 to 3:1. Preferably, the ratio is about 1:10 to 2:1. Most preferably, the ratio is 1:10 to 1.5:1. The active ingredient is present in an effective amount, which typically is about 0.1 mg to about 1000 mg per unit dose.

The medicament may be prepared by using techniques and methods known in the art. For example, the coating composition of the present invention may be applied onto one or more granules or particles of the active ingredient or medicine by using a fluidized bed coating operation. The coated granules or particles may then be processed into a pharmaceutically acceptable dosage form.

The coated medicament can be, for example, chewable tablets, powders for reconstituted suspensions, regular liquid form of prepared suspensions, fast dissolving quick melt tablets, lozenges, wafers, chewing gums, hard shell gelatin capsules with powder/granules/liquid fills, soft shell gelatin with liquid center or filled with powder or granules, regular compressed tablets with immediate or delayed release, candy and candy bar forms, aerosol creams and gels.

Many pharmaceutically active ingredients can be coated with the taste masking system of the present invention. For example, the taste masking system can be applied to analgesics such as acetaminophen, aspirin, ibuprofen, dexibuprofen lysinate, naproxen, ketoprofen; antibiotics such as lactams, quinolones, macrolides and salts thereof; gastrointestinal drugs such as loperamide, famotidine, ranitidine, cimetidine and salts thereof; cardio vascular agents such as ibersartan, captopril, lisinopril and salts thereof; CNS drugs such as nefzodone, aeripriprazole, buspirone and salts thereof; antihistamines such as chlorpheniramine and astemizole; decongestants such as pseudoephedrine; antivirals; anticancer; antiplatelet; vitamins; minerals; psyllium; or mixtures thereof. The pharmaceutically active agent is present in an amount effective for the treatment of the condition for which it is intended, typically and preferably as set forth in the Physician's Desk Reference, 53rd edition, incorporated herein by reference thereto.

To illustrate the present invention, the following examples are provided. However, it should be understood that the present invention is not limited to the examples described.

In the examples provided, medicinal tablets were prepared as follows: (1) granules or crystals of a drug ingredient were coated with a coating composition in a fluid bed coater, (2) the coated granules or crystals were then combined with ingredients commonly used in making chewable/fast melting tablets and/or dry suspensions such as sugars, sweetners, and flavors, (3) the mixture was then compressed into tablet form to a hardness of about 10 Strong-Cobb units, using 11/16 inch round flat tooling. Each tablet had a weight of about 1550 mg.

Taste masking effectiveness is difficult to quantify. As set forth above, taste masking is understood to mean herein a perceived reduction of an undesirable taste that would otherwise be present. The examples demonstrate the taste masking benefits of the present invention, by measuring the percentage of a drug ingredient dissolved over a period of time under different pH conditions, and by product tasting.

EXAMPLE 1

Example 1 provides the results of dissolution testing performed on medicinal tablets made from granules of acetominophen (APAP) coated with one of three type coating compositions. The three types of medicinal tablets were prepared compressing granules coated with the coating composition. The three types of medicinal tablets (a–c) were prepared by tableting granules having the following coatings (a) 60% cellulose acetate:40% Eudragit E® 100:(0% triethanolamine), (b) 60% cellulose acetate:38% Eudragit E® 100:2% triethanolamine, or (c) 60% cellulose acetate:32% Eudragit E® 100:8% triethanolamine.

Table 1 summarizes the results of an experiment performed to evaluate the percent of a drug ingredient dissolved over a given period of time in an environment where the pH is about 7, i.e. conditions similar to the mouth. Medicinal tablets (a), (b), and (c) were tested. The medicinal tablets were placed in a buffer solution having a pH of 7, and the percent APAP dissolved was measured at given time intervals.

TABLE 1

Dissolution of APAP in a 7.0 pH Buffer
Formulation Ratio Of
Cellulose Acetate:Eudragit ® E 100:Triethanolamine

| TIME (min) | 60:40:0 | 60:38:2 | 60:32:8 |
|---|---|---|---|
| 0 | 0 | 0 | 0 |
| 1 | 7.1 | 10.3 | 6.4 |
| 6 | 68.8 | 62.4 | 44.5 |
| 11 | 80.3 | 76.3 | 59.4 |
| 16 | 86.2 | 83.2 | 68.4 |
| 21 | 89.8 | 87.5 | 74.4 |
| 26 | 92.3 | 90.4 | 78.6 |

The results indicate that in an environment where the pH is about 7, medicinal tablets (a) showed a higher percentage of the drug ingredient dissolved in a given period of time than medicinal tablets (b) and (c), which have triethanolamine in the coating composition. Since medicinal tablets (b) and (c) showed lower percentages of the drug ingredient dissolved, less of the drug ingredient was available to taste. This demonstrates that the coating composition of the present invention inhibits the availability of the drug ingredient and thereby provides an effective means for masking the undesirable taste of a drug ingredient such as APAP under neutral pH conditions.

Table 2 summarizes the results of an experiment performed to evaluate the percent of a drug ingredient dissolved over a given period of time, when medicinal tablets (a), (b), and (c) were placed in a buffer solution having a pH of 1.2, i.e. a condition similar to the stomach. The percent APAP dissolved was measured at specific time intervals.

TABLE 2

Dissolution of APAP in a 1.2 pH Buffer
Formulation Ratio Of
Cellulose Acetate:Eudragit ® E 100:Triethanolamine

| TIME (min) | 60:40:0 | 60:38:2 | 60:32:8 |
|---|---|---|---|
| 0 | 0 | 0 | 0 |
| 1 | 10.9 | 16.6 | 19.3 |
| 6 | 83.8 | 93.4 | 94 |
| 11 | 96.1 | 97.7 | 100.2 |
| 16 | 97.7 | 99.8 | 101.4 |
| 21 | 98.3 | 100.2 | 101.8 |
| 26 | 98.5 | 100.4 | 102 |

In an acidic environment, namely a pH of 1.2, results showed that medicinal tablets (b) and (c), had a higher percentage of the drug ingredient dissolved in a given period of time. This demonstrates that the medicine trapped beneath the coating is released more rapidly into the body. However, medicinal tablet (a), which does not have triethanolamine showed a lower percentage of drug ingredient dissolved in the same time period.

EXAMPLE 2

Acetaminophen in the crystalline form having a mesh size about 40 to 80, was coated with a coating composition of 60% cellulose acetate:28% Eudragit E 100:12% triethanolamine. The same coating composition was applied as a coating for granular caffeine that was also about 40 to 80 mesh size. The coating thickness was varied and the coated crystals and granules were formed into medicinal tablets.

Tables 3 and 5 show the percentage of the drug ingredient that dissolved in a neutral environment with a pH of 7. Tables 4 and 6 show the percentage of the drug ingredient that dissolved in an acidic environment with a pH of 1.2.

TABLE 3

Coated Acetaminophen Tablet - Dissolution Rate
in a 7.0 pH Buffer
Formulation Ratio Of
Cellulose Acetate:Eudragit ® E 100:Triethanolamine
60:28:12
Coating Thickness Applied

| TIME (min) | 20% Add On | 30% Add On | 40% Add On |
|---|---|---|---|
| 0 | 0 | 0 | 0 |
| 1 | 2.2 | 1.3 | 1.1 |
| 6 | 12.8 | 7.6 | 8.2 |
| 11 | 18.1 | 10.4 | 10.9 |
| 16 | 22.6 | 12.8 | 13 |
| 21 | 27 | 15 | 14.9 |
| 26 | 31.4 | 17.3 | 16.5 |
| 31 | 35.6 | 19.5 | 18.2 |
| 36 | 39.7 | 21.5 | 19.8 |

TABLE 4

Coated Acetaminophen Tablet - Dissolution Rate
in a 1.2 pH Buffer
Formulation Ratio Of
Cellulose Acetate:Eudragit ® E 100:Triethanolamine
60:28:12
Coating Thickness Applied

| TIME (min) | 20% Add On | 30% Add On | 40% Add On |
|---|---|---|---|
| 0 | 0 | 0 | 0 |
| 1 | 3.6 | 2 | 2.2 |
| 6 | 33.5 | 20.6 | 22.2 |
| 11 | 58.4 | 36.1 | 35.4 |
| 16 | 78.9 | 52.1 | 48.7 |
| 21 | 91.4 | 68.1 | 61.8 |
| 26 | 97.3 | 80.3 | 73.8 |
| 31 | 99.8 | 88 | 83.3 |
| 36 | 100.8 | 92.3 | 89.9 |

TABLE 5

Coated Caffeine Tablet - Dissolution Rate
in a 7.0 pH Buffer
Formulation Ratio Of
Cellulose Acetate:Eudragit ® E 100:Triethanolamine
60:28:12
Coating Thickness Applied

| TIME (min) | 20% Add on | 30% Add on | 40% Add on |
|---|---|---|---|
| 0 | 0 | 0 | 0 |
| 1 | 2.8 | 1.2 | 1.1 |
| 6 | 12.8 | 7.5 | 7.5 |
| 11 | 22.4 | 11.3 | 10 |
| 16 | 30.3 | 14.8 | 12 |
| 21 | 37.4 | 17.6 | 13.9 |
| 26 | 44.2 | 21.4 | 14.9 |
| 31 | 50.4 | 24.5 | 17.2 |
| 36 | 55.8 | 27.6 | 18.5 |

TABLE 6

Coated Caffeine Tablet - Dissolution Rate
in a 1.2 pH Buffer
Formulation Ratio Of
Cellulose Acetate:Eudragit ® E 100:Triethanolamine
60:28:12
Coating Thickness Applied

| TIME (min) | 20% Add on | 30% Add on | 40% Add on |
|---|---|---|---|
| 0 | 0 | 0 | 0 |
| 1 | 2.8 | 1.5 | 1.9 |
| 6 | 37.1 | 19 | 17.3 |
| 11 | 72.8 | 42 | 34.3 |
| 16 | 91.4 | 64.7 | 53.4 |
| 21 | 98 | 82.1 | 70.7 |
| 26 | 100.8 | 90.2 | 83.8 |
| 31 | 101.7 | 94.2 | 92.4 |
| 36 | 102.4 | 96 | 97.3 |

The results presented in the above tables show that in an environment where the pH is 7, the 20% add on coating dissolves slightly faster than the 30% and 40% add on coatings. In an acidic environment where the pH is 1.2, similar results are obtained, where the 20% add on coating dissolves slightly faster than the 30% and 40% add on coatings.

This confirms that the coating thickness does affect the dissolution rate of the drug ingredient and it also demonstrates how the taste masking effect can be varied by adjusting the thickness of the coating composition of the present invention.

EXAMPLE 3

Table 7 summarizes the results of a storage study performed to evaluate the taste masking effectiveness of a dry suspension. The suspension was prepared by coating granules of caffeine with the coating composition of the present invention. The dry suspension was held at room temperature for a period of five days. The percent free caffeine (% Free), i.e. the percent of caffeine available, was determined and the taste of the dry suspension was evaluated.

TABLE 7

STORAGE DATA: 5 DAYS AT ROOM TEMPERATURE

| DAY | % FREE | TASTE |
|---|---|---|
| 0 | 2.47% | NOT BITTER |
| 3 | 9.87% | NOT BITTER |
| 4 | 9.17% | NOT BITTER |
| 5 | 8.28% | NOT BITTER |

The results indicate that the suspension coated with the coating composition of the present invention does not have a bitter taste, which is characteristically found in caffeine. In contrast, a suspension formulated using uncoated caffeine, will dissolve immediately in water once the suspension was formed. Such immediate dissolution provided a bad or unacceptable taste as it is consumed.

Having thus described the present invention with particular reference to preferred embodiments thereof, it will be apparent that various changes and modifications may be made therein without departing from the spirit and scope of the present invention as defined in the appended claims.

What is claimed is:

1. A coating composition for masking the taste of a drug active ingredient or medicine and enhancing release of the drug or medicine in the stomach, comprising:

an effective amount of a taste masking blend of
(a) dimethylaminoethyl methacrylate and neutral methacrylic acid ester;
(b) a cellulose ester polymer; and
(c) about 0.2 wt. % to about 20 wt. % of an alkaline modifier selected from the group consisting of triethanolamine, basic amino acids, talc, ammonium oleate, meglumine, trimethylamine, calcium silicate, aluminum magnesium silicate, food alkalizing agent, and mixture thereof; wherein the amount of alkaline modifier is based on the total weight of the composition, and to increase the coating composition's dissolution rate in the stomach, as compared to a like coating composition that does not contain the alkaline modifier.

2. The composition of claim 1, wherein said dimethylaminoethyl methacrylate and neutral methacrylic acid ester blend is about 3 wt. % to about 97 wt. % of the total weight of the composition.

3. The composition of claim 1, wherein said cellulose ester polymer is selected from the group consisting of cellulose acetate, cellulose acetate butyrate, cellulose acetate triacetate, ethyl cellulose, and mixtures thereof.

4. The composition of claim 1, wherein said cellulose ester polymer is about 3 wt. % to about 97 wt. % of the total weight of the composition.

5. The composition of claim 1, wherein said alkaline modifier is triethanolamine.

6. The composition of claim 1, wherein said alkaline modifier is about 1 wt. % to about 15 wt. % of the total weight of the composition.

7. The composition of claim 1, further comprising an additive selected from the group consisting of 2-vinyl pyridine (V)/styrene (S) copolymer.

8. The composition of claim 1, further comprising one or more optional ingredients selected from the group consisting of diluents, fillers, bulking agents, pigments, opacifiers, other plasticizers, and mixtures thereof.

9. A medicament composition comprising:
a drug ingredient; and
a coating composition for masking the taste of the drug ingredient, the drug ingredient being coated by the coating composition, the coating composition comprising:
an effective amount of a taste masking blend of
(a) dimethylaminoethyl methacrylate and neutral methacrylic acid ester;
(b) a cellulose ester polymer; and
(c) about 0.2 wt. % to about 20 wt. % of an alkaline modifier selected from the group consisting of triethanolamine, basic amino acids, talc, ammonium oleate, meglumine, trimethylamine, calcium silicate, aluminum magnesium silicate, food alkalizing agent, and mixture thereof; wherein the amount of alkaline modifier is based on the total weight of the composition, and to increase the dissolution rate of the coating in the stomach, as compared to a like coating composition that does not contain the alkaline modifier.

10. The medicament composition of claim 9, wherein the drug ingredient is selected from the group consisting of particles, granules, powders, and mixtures thereof.

11. The medicament composition of claim 9, wherein said dimethylaminoethyl methacrylate and neutral methacrylic acid ester is about 3 wt. % to about 97 wt. % of the total weight of the composition.

12. The medicament composition of claim 9, wherein said cellulose ester polymer is selected from the group consisting of cellulose acetate, cellulose acetate butyrate, cellulose acetate triacetate, ethyl cellulose, and mixtures thereof.

13. The medicament composition of claim 9, wherein said cellulose ester polymer is about 3 wt. % to about 97 wt. % of the total weight of the composition.

14. The medicament composition of claim 9, wherein said alkaline modifier is triethanolamine.

15. The medicament composition of claim 9, wherein said alkaline modifier is about 1 wt. % to about 15 wt. % of the total weight of the composition.

16. The medicament composition of claim 9, wherein the drug ingredient is selected from the group consisting of acetaminophen, aspirin, ibuprofen, dexibuprofen lysinate, naproxen, ketoprofen, lactam, quinolone, macrolide or salts thereof, loperamide, famotidine, ranitidine, cimetidine and salts thereof, ibersartan, captopril, lisinopril or salts thereof, nefzodone, buspirone or salts thereof, chlorpheniramine, astemizole, pseudoephedrine, antivirals, anticancer, antiplatelet, vitamins, minerals, psyllium, and mixtures thereof.

17. The medicament composition of claim 9, wherein the medicament composition is selected from the group consisting of: chewable tablets, powders for reconstituted suspensions, regular liquid form of prepared suspensions, fast dissolving quick melt tablets, lozenges, wafers, chewing gums, hard shell gelatin capsules with powder/granules/liquid fills, soft shell gelatin with liquid center or filled with powder or granules, regular compressed tablets with immediate or delayed release, candy or candy bar forms, aerosol creams, and gels.

18. The medicament composition of claim 9, wherein the medicament composition is a tablet formed by compressing coated granules.

19. The medicament composition of claim 9, wherein the medicament composition has a ratio of coating composition to drug ingredient that is about 1:50 to 3:1.

20. The medicament composition of claim 19, wherein said ratio is about 1:10 to 2:1.

21. The medicament composition of claim 9, wherein said coating composition effectively masks the taste of the drug ingredient.

22. The composition of claim 1, wherein, when the drug active ingredient is coated with the composition, the alkaline modifier is present in the coating in an amount sufficient to effect substantially complete release of the drug active ingredient in the stomach.

23. The composition of claim 9, wherein the alkaline modifier, in the coating composition coating the drug ingredient, is present in an amount sufficient to effect substantially complete release of the drug active ingredient in the stomach.

* * * * *